US012697079B2

(12) United States Patent　　　　　　(10) Patent No.:　　US 12,697,079 B2
Zhan et al.　　　　　　　　　　　　　　(45) Date of Patent:　　　Aug. 4, 2026

(54) OVERLAPPING PIXEL SUMMING SCHEME IN THE FULL SIZE PHOTON COUNTING COMPUTED TOMOGRAPHY (CT)

(71) Applicant: Canon Kabishiki Kaisha, Tokyo (JP)

(72) Inventors: Xiaohui Zhan, Vernon Hills, IL (US);
Ilmar Hein, Vernon Hills, IL (US);
Ruoqiao Zhang, Vernon Hills, IL (US)

(73) Assignee: Canon Kabushiki Kaisha, Tokyo (JP)

( * ) Notice: Subject to any disclaimer, the term of this patent is extended or adjusted under 35 U.S.C. 154(b) by 375 days.

(21) Appl. No.: 17/862,624

(22) Filed: Jul. 12, 2022

(65) Prior Publication Data

US 2024/0016459 A1　　　Jan. 18, 2024

(51) Int. Cl.
| *A61B 6/03* | (2006.01) |
| *A61B 6/42* | (2024.01) |
| *G01T 1/17* | (2006.01) |
| *G01T 1/24* | (2006.01) |
| *G01T 1/29* | (2006.01) |

(52) U.S. Cl.
CPC ............ *A61B 6/4241* (2013.01); *A61B 6/032* (2013.01); *A61B 6/4233* (2013.01); *G01T 1/17* (2013.01); *G01T 1/247* (2013.01); *G01T 1/2985* (2013.01)

(58) Field of Classification Search
CPC ...................................... A61B 6/032
See application file for complete search history.

(56) References Cited

U.S. PATENT DOCUMENTS

| 2013/0310655 | A1* | 11/2013 | Sachs ..................... A61B 5/055 600/301 |
| 2014/0138553 | A1 | 5/2014 | Ogawa et al. |
| 2016/0334520 | A1* | 11/2016 | Flohr ...................... G06T 12/30 |
| 2017/0244910 | A1* | 8/2017 | Karim ....................... G01T 1/24 |
| 2018/0196149 | A1* | 7/2018 | Blevis .................... G01T 1/243 |

(Continued)

FOREIGN PATENT DOCUMENTS

| EP | 3 420 722 | 1/2019 |
| WO | 2022/066376 A1 | 3/2022 |

OTHER PUBLICATIONS

Extended European Search Report issued Nov. 24, 2023 in European Patent Application No. 23185121.3, 10 pages.

(Continued)

*Primary Examiner* — Uzma Alam
*Assistant Examiner* — Shun Lee
(74) *Attorney, Agent, or Firm* — Oblon, McClelland, Maier & Neustadt, L.L.P.

(57)　　　　　　　ABSTRACT

A photon counting detector (PCD) apparatus includes a PCD array including a plurality of micro-pixels positioned in at least one of a channel direction and a row direction; and processing circuitry configured to: receive signals from each of the plurality of micro-pixels; configure the PCD array to include (a) a first micro-pixel area including a first group of plural micro-pixels of the plurality of micro-pixels and (b) a second micro-pixel area including a second group of plural micro-pixels of the plurality of micro-pixels, such that a portion of the first and second groups of plural micro-pixels overlap between the first and second groups; bin the signals from the first group of plural micro-pixels into a first virtual bin value; and bin the signals from the second group of plural micro-pixels into a second virtual bin value.

21 Claims, 9 Drawing Sheets

(56) References Cited

U.S. PATENT DOCUMENTS

| | | |
|---|---|---|
| 2019/0056517 A1* | 2/2019 | Alving .................... G01T 1/244 |
| 2019/0114746 A1 | 4/2019 | Sakumura et al. |
| 2020/0069266 A1 | 3/2020 | Cai et al. |
| 2021/0186439 A1 | 6/2021 | Goederer et al. |
| 2021/0186440 A1 | 6/2021 | Kreisler et al. |
| 2023/0136957 A1 | 5/2023 | Goederer et al. |

OTHER PUBLICATIONS

Third Party Patentability Search Report issued Jul. 20, 2022, in U.S. Appl. No. 17/825,650, 20 pages.

Oliver L. P. Pickford Scienti et al.; "CdTe Based Energy Resolving, X-ray Photon Counting Detector Performance Assessment: The Effects of Charge Sharing Correction Algorithm Choice", Joint Department of Physics, Institute of Cancer Research and Royal Marsden NHS Foundation Trust; Oct. 27, 2020.

Office Action issued Sep. 16, 2025, in corresponding European Patent Application No. 23185121.3, herein, 8 pages.

* cited by examiner

FIG. 1

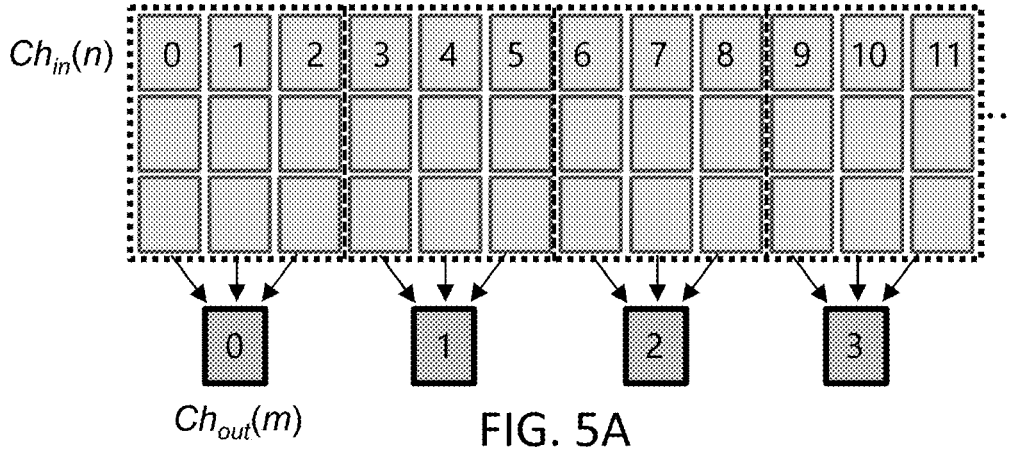
$Ch_{in}(n)$
$Ch_{out}(m)$
FIG. 5A
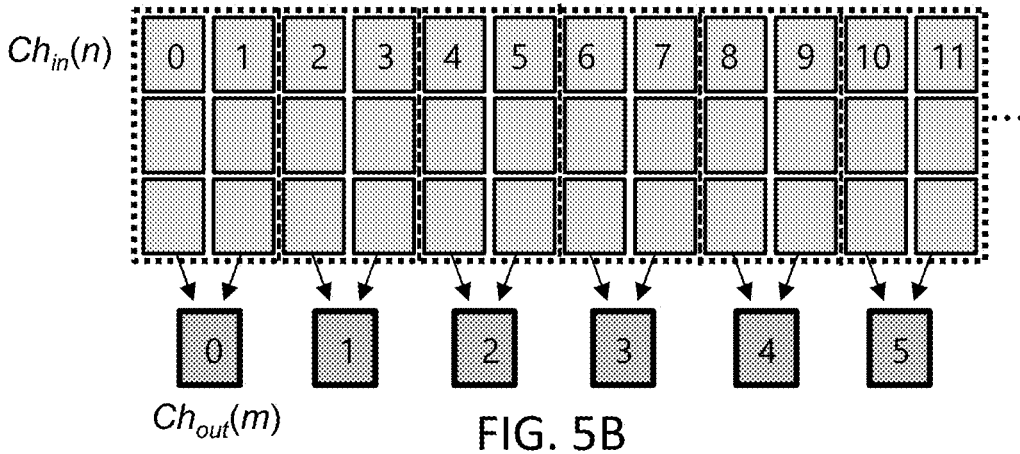
$Ch_{in}(n)$
$Ch_{out}(m)$
FIG. 5B
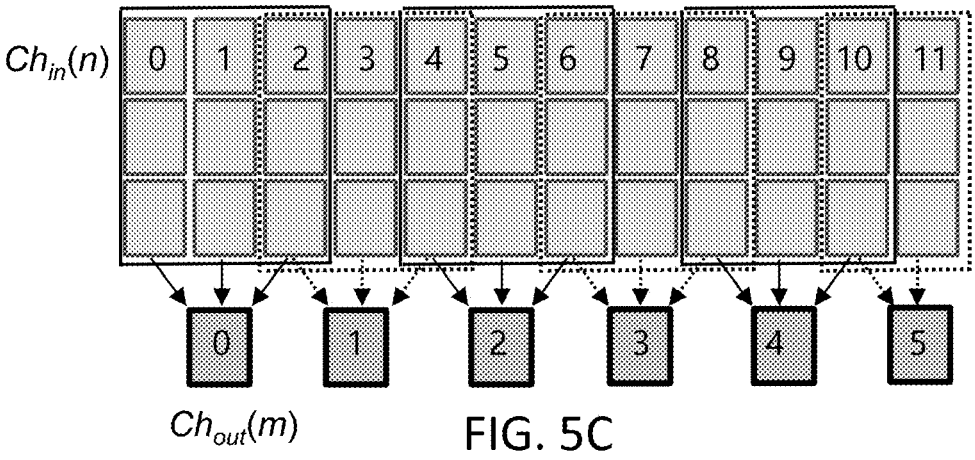
$Ch_{in}(n)$
$Ch_{out}(m)$   FIG. 5C

OVERLAPPING PIXEL SUMMING SCHEME IN THE FULL SIZE PHOTON COUNTING COMPUTED TOMOGRAPHY (CT)

FIELD OF THE INVENTION

The disclosure relates to configurable pixel summing in a photon counting computed tomography system, and in one embodiment to a photon counting detector (PCD) apparatus including a dynamically configurable a PCD array including a plurality of micro-pixels positioned in at least one of a channel direction and a row direction, wherein first and second groups of micro-pixels overlap in at least one of the channel and row directions.

DESCRIPTION OF THE RELATED ART

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/ or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response resulting in a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor-based detector using direct conversion is designed to resolve the energy of the individual incoming photons and generate measurement of multiple energy bin counts for each integration period. However, due to the detection physics in such semiconductor materials (e.g. CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to sensor material non-uniformity and complexity of the integrated detection system, it is impossible to do accurate modeling of such detector response for a PCD just based on physics theories or Monte Carlo simulations with a certain modeling of the signal induction process, which modeling determines the accuracy of the forward model of each measurement. Also, due to uncertainties in the incident X-ray tube spectrum modeling, the modelling introduces additional errors in the forward model, and all these factors eventually degrade the material decomposition accuracy from the PCD measurements, therefore the generated spectral images.

A typical PCD detector utilizes a much smaller pixel size than a conventional scintillator based energy-integrating detector (EID). The size of the PCD pixel is usually chosen by balancing the charge-sharing effect, which is more prominent with the smaller size, and the pulse pileup effect, which is more severe with the larger pixel size (higher count rate). The smaller pixel design naturally enables various summing schemes which will result in images with different spatial resolutions. Intuitively, a larger summing size results in poorer spatial resolution but lower noise; and a smaller summing size with better spatial resolution but higher noise.

In practice, the effective detection area per detector pitch is further affected by the shadow of anti-scatter-grids. Therefore, the measurement count rate can still significantly vary across the pixels under uniform incident flux, which increases the complexity of detector response modeling as well as the difficulty in the calibration design. The existence of bad pixels in the detector can further degrade image quality. How to mitigate these problems and still generate optimal image quality is a practical problem in PCD system development.

SUMMARY

The embodiments presented herein relate to an apparatus and a method for overlapping pixel summing. A photon counting detector (PCD) apparatus includes, but is not limited to, (a) a PCD array including a plurality of micro-pixels positioned in at least one of a channel direction and a row direction; and (b) processing circuitry configured to: (b1) receive signals from each of the plurality of micro-pixels, (b2) configure the PCD array to include (b1a) a first micro-pixel area including a first group of plural micro-pixels of the plurality of micro-pixels and (b1b) a second micro-pixel area including a second group of plural micro-pixels of the plurality of micro-pixels, such that a portion of the first and second groups of plural micro-pixels overlap between the first and second groups, (b3) bin the signals from the first group of plural micro-pixels into a first virtual bin value; and (b4) bin the signals from the second group of plural micro-pixels into a second virtual bin value.

An overlapping micro-pixel summing method includes, but is not limited to, (a) configuring a PCD array including a plurality of micro-pixels positioned in at least one of a channel direction and a row direction to include (a1) a first micro-pixel area including a first group of plural micro-pixels of the plurality of micro-pixels and (a2) a second micro-pixel area including a second group of plural micro-pixels of the plurality of micro-pixels, such that a portion of the first and second groups of plural micro-pixels overlap between the first and second groups, (b) receiving signals from each of the plurality of micro-pixels, (c) binning the signals from the first group of plural micro-pixels into a first virtual bin value; and (d) binning the signals from the second group of plural micro-pixels into a second virtual bin value.

In at least one embodiment, the PCD apparatus and the micro-pixel summing method are utilized as part of a CT scanner.

BRIEF DESCRIPTION OF THE DRAWINGS

The application will be better understood in light of the description which is given in a non-limiting manner, accompanied by the attached drawings in which:

FIG. 1 is a block diagram of an exemplary configuration of an X-ray CT apparatus imaging a person as a subject according to an exemplary embodiment described below.

FIGS. 5A-5C depict the differences in channel output for the standard binning, asymmetrical standard binning, and binning with overlap in the channel direction.

DETAILED DESCRIPTION OF THE PREFERRED EMBODIMENTS

Figure 2:
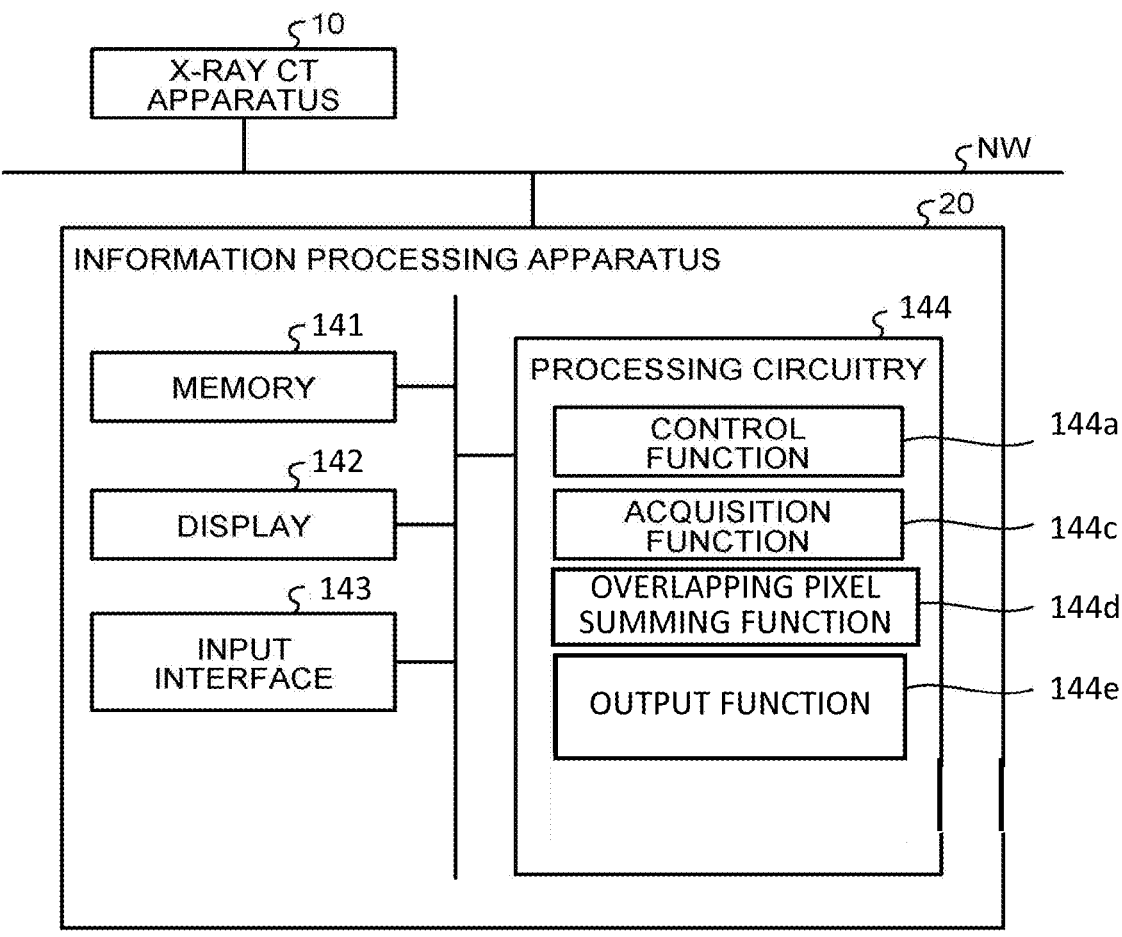
FIG. 2 is a block diagram of an exemplary configuration of information processing apparatus connected to an X-ray CT apparatus according to another exemplary embodiment described below.

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

An X-ray CT will be described as an example of a medical image diagnostic modality herein. In that context, an information processing method of information acquired by imaging performed by the X-ray CT will be described.

Figure 1:
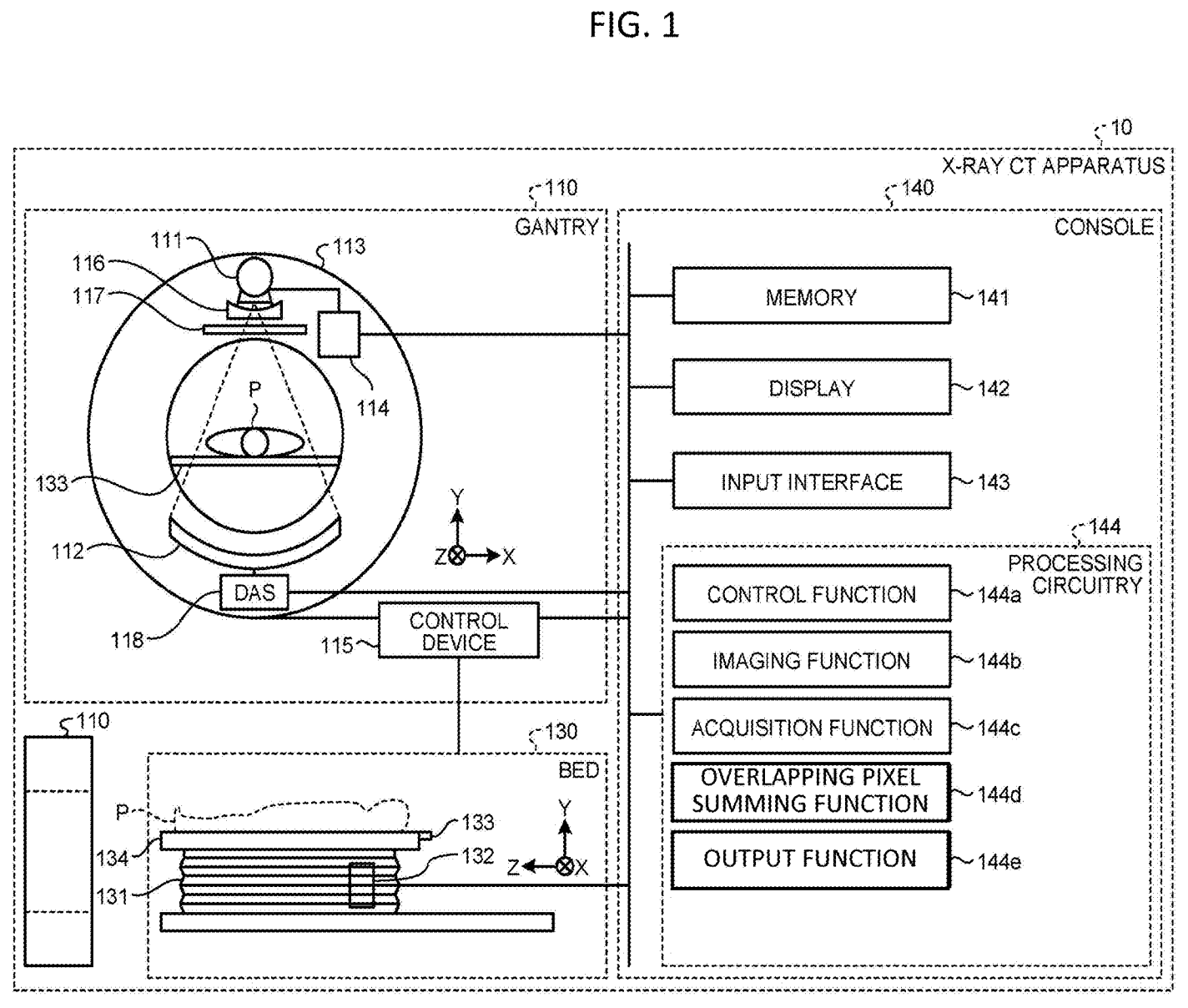

The X-ray CT is implemented, for example, in an X-ray CT apparatus 10 illustrated in FIG. 1. FIG. 1 is a block diagram illustrating an example of a configuration of the X-ray CT apparatus 10 according to a first embodiment. For example, the X-ray CT apparatus 10 has a gantry 110, a bed 130, and a console 140.

In FIG. 1, it is assumed that the longitudinal direction of a rotating shaft of a rotating frame 113 or a tabletop 133 of the bed 130 in a non-tilted state is a Z axis direction.

Furthermore, it is assumed that an axial direction orthogonal to the Z axis direction and horizontal to a floor surface is an X axis direction. Furthermore, it is assumed that an axial direction orthogonal to the Z axis direction and perpendicular to the floor surface is a Y axis direction. Note that FIG. 1 illustrates the gantry 110 drawn from a plurality of directions for convenience of description and the X-ray CT apparatus 10 has one gantry 110.

The gantry 110 includes an X-ray tube 111, an X-ray detector 112, the rotating frame 113, an X-ray high voltage device 114, a control device 115, a wedge 116, a collimator 117, and a data acquisition system (DAS) 118.

The X-ray tube 111 is a vacuum tube having a cathode (filament) that generates thermoelectrons and an anode (target) that generates X-rays in response to a collision of thermoelectrons. The X-ray tube 111 emits the thermoelectrons toward the anode from the cathode by the application of a high voltage from the X-ray high voltage device 114, thereby generating the X-rays to be emitted to a subject P.

The X-ray detector 112 detects the X-rays emitted from the X-ray tube 111 and passed through the subject P, and outputs a signal corresponding to the dose of the detected X-rays to the DAS 118. The X-ray detector 112, for example, includes a plurality of detection element arrays in which a plurality of detection elements are arranged in a channel direction (channel direction) along one arc centered on a focal point of the X-ray tube 111. The X-ray detector 112, for example, has a structure in which the detection element arrays with the detection elements arranged in the channel direction are arranged in a row direction (slice direction and row direction).

For example, the X-ray detector 112 is an indirect conversion type detector having a grid, a scintillator array, and a photosensor array. The scintillator array has a plurality of scintillators. Each of the scintillators has a scintillator crystal that outputs light with a photon quantity corresponding to an incident X-ray dose. The grid has an X-ray shielding plate that is disposed on the surface of the scintillator array on an X-ray incident side and absorbs scatted X-rays. The grid may also be referred to as a collimator (a one-dimensional collimator or a two-dimensional collimator). The photosensor array has a function of converting light into an electrical signal corresponding to the amount of light from the scintillator, and has, for example, photosensors such as photodiodes. Note that the X-ray detector 112 may be a direct conversion type detector having a semiconductor element that converts the incident X-rays into electrical signals.

The rotating frame 113 is an annular frame that supports the X-ray tube 111 and the X-ray detector 112 so as to face each other and rotates the X-ray tube 111 and the X-ray detector 112 by the control device 115. For example, the rotating frame 113 is a casting made of aluminum. Note that the rotating frame 113 can further support the X-ray high voltage device 114, the wedge 116, the collimator 117, the DAS 118 and the like, in addition to the X-ray tube 111 and the X-ray detector 112. Moreover, the rotating frame 113 can further support various configurations not illustrated in FIG. 1. Hereinafter, in the gantry 110, the rotating frame 113 and a part, which rotationally moves with the rotating frame 113, are also referred to as a rotating part.

The X-ray high voltage device 114 has electric circuitry such as a transformer and a rectifier, and has a high voltage generation device that generates a high voltage to be applied to the X-ray tube 111 and an X-ray control device that controls an output voltage corresponding to the X-rays generated by the X-ray tube 111. The high voltage generation device may be a transformer type device or an inverter type device. Note that the X-ray high voltage device 114 may be provided on the rotating frame 113, or may also be provided on a fixed frame (not illustrated).

The control device 115 has processing circuitry having a central processing unit (CPU) and the like, and a driving mechanism such as a motor and an actuator. The control device 115 receives input signals from an input interface 143 and controls the operations of the gantry 110 and the bed 130. For example, the control device 115 controls the rotation of the rotating frame 113, the tilt of the gantry 110, the operation of the bed 130, and the like. As an example, as control for tilting the gantry 110, the control device 115 rotates the rotating frame 113 around an axis parallel to the X axis direction based on information on an input inclination angle (tilt angle). Note that the control device 115 may be provided in the gantry 110 or may also be provided in the console 140.

The wedge 116 is an X-ray filter for adjusting the dose of the X-rays emitted from the X-ray tube 111. Specifically, the wedge 116 is an X-ray filter that attenuates the X-rays emitted from the X-ray tube 111 such that the X-rays emitted from the X-ray tube 111 to the subject P have a predetermined distribution. For example, the wedge 116 is a wedge filter or a bow-tie filter and is manufactured by processing aluminum and the like to have a predetermined target angle and a predetermined thickness.

The collimator 117 is a lead plate and the like for narrowing down the emission range of the X-rays having transmitted through the wedge 116 and forms a slit by a combination of a plurality of lead plates and the like. Note that the collimator 117 may also be referred to as an X-ray diaphragm. Furthermore, although FIG. 1 illustrates a case where the wedge 116 is disposed between the X-ray tube 111 and the collimator 117, the collimator 117 may be disposed between the X-ray tube 111 and the wedge 116. In such a case, the wedge 116 attenuates the X-rays, which are emitted from the X-ray tube 111 and whose emission range is limited by the collimator 117, by allowing the X-rays to pass therethrough.

The DAS 118 acquires X-ray signals detected by each detector element included in the X-ray detector 112. For example, the DAS 118 has an amplifier that performs an amplification process on electrical signals output from each detector element and an A/D converter that converts the electrical signals to digital signals, and generates detection data. The DAS 118 is implemented by, for example, a processor.

The data generated by the DAS 118 is transmitted from a transmitter having a light emitting diode (LED) provided on the rotating frame 113 to a receiver having a photodiode provided on a non-rotating part (for example, a fixed frame and the like and not illustrated in FIG. 1) of the gantry 110 by optical communication, and is transmitted to the console 140. The non-rotating part is, for example, a fixed frame and the like that rotatably supports the rotating frame 113. Note that the data transmission method from the rotating frame 113 to the non-rotating part of the gantry 110 is not limited to the optical communication, and may adopt any non-contact type data transmission method or a contact type data transmission method.

The bed 130 is a device that places and moves the subject P to be scanned and includes a pedestal 131, a couch driving device 132, the tabletop 133, and a support frame 134. The pedestal 131 is a casing that supports the support frame 134 so as to be movable in a vertical direction. The couch driving device 132 is a driving mechanism that moves the tabletop 133, on which the subject P is placed, in a long axis direction of the tabletop 133 and includes a motor, an actuator and the like. The tabletop 133 provided on the upper surface of the support frame 134 is a plate on which the subject P is placed. Note that the couch driving device 132 may also move the support frame 134 in the long axis direction of the tabletop 133 in addition to the tabletop 133.

The console 140 has a memory 141, a display 142, the input interface 143, and processing circuitry 144. Although the console 140 is described as a separate body from the gantry 110, the gantry 110 may include the console 140 or a part of each component of the console 140.

The memory 141 is implemented by, for example, a semiconductor memory element such as a random access memory (RAM) and a flash memory, a hard disk, an optical disk, and the like. For example, the memory 141 stores a computer program for circuitry included in the X-ray CT apparatus 10 to perform its functions. Furthermore, the memory 141 stores various information obtained by imaging the subject P. Note that the memory 141 may be implemented by a server group (cloud) connected to the X-ray CT apparatus 10 via a network.

The display 142 displays various information. For example, the display 142 displays an image based on the imaging described herein. Furthermore, for example, the display 142 displays a graphical user interface (GUI) for receiving various instructions, settings, and the like from a user via the input interface 143. For example, the display 142 is a liquid crystal display or a cathode ray tube (CRT) display. The display 142 may be a desktop type display, or may be composed of a tablet terminal and the like capable of wirelessly communicating with the body of the X-ray CT apparatus 10.

Although the X-ray CT apparatus 10 is described as including the display 142 in FIG. 1, the X-ray CT apparatus 10 may include a projector instead of or in addition to the display 142. Under the control of the processing circuitry 144, the projector can perform projection onto a screen, a wall, a floor, the body surface of the subject P, and the like. As an example, the projector can also perform projection onto any plane, object, space, and the like by projection mapping.

The input interface 143 receives various input operations from a user, converts the received input operations into electrical signals, and outputs the electrical signals to the processing circuitry 144. For example, the input interface 143 is implemented by a mouse, a keyboard, a trackball, a switch, a button, a joystick, a touch pad for performing an input operation by touching an operation surface, a touch screen in which a display screen and a touch pad are integrated, non-contact input circuitry using an optical sensor, voice input circuitry, and the like. Note that the input interface 143 may be composed of a tablet terminal and the like capable of wirelessly communicating with the body of the X-ray CT apparatus 10. Furthermore, the input interface 143 may be circuitry that receives an input operation from a user by motion capture. As an example, the input interface 143 can receive a user's body movement, line of sight, and the like as an input operation by processing a signal acquired via a tracker or an image collected for a user. Furthermore, the input interface 143 is not limited to one including physical operation parts such as a mouse and a keyboard. For example, an example of the input interface 143 includes electric signal processing circuitry which receives an electric signal corresponding to an input operation from an external input device separately provided from the X-ray CT apparatus 10 and outputs the electric signal to the processing circuitry 144.

The processing circuitry 144 controls the overall operation of the X-ray CT apparatus 10 by performing a control function 144a, an imaging function 144b, an acquisition function 144c, an overlapping pixel summing function 144d, and an output function 144e.

For example, the processing circuitry 144 reads a computer program corresponding to the control function 144a from the memory 141 and executes the read computer program, thereby controlling various functions, such as the imaging function 144b, the acquisition function 144c, the overlapping pixel summing function 144d, and the output function 144e, based on various input operations received from a user via the input interface 143.

Furthermore, for example, the processing circuitry 144 reads a computer program corresponding to the imaging function 144b from the memory 141 and executes the read computer program, thereby imaging the subject P. For example, the imaging function 144b controls the X-ray high voltage device 114 to supply the X-ray tube 111 with a high voltage. With this, the X-ray tube 111 generates X-rays to be emitted to the subject P. Furthermore, the imaging function 144b controls the couch driving device 132 to move the subject P into an imaging port of the gantry 110. Furthermore, the imaging function 144b adjusts the position of the wedge 116 and the opening degree and position of the collimator 117, thereby controlling the distribution of the X-rays emitted to the subject P. Furthermore, the imaging function 144b controls the control device 115 to rotate the rotating part. Furthermore, while the imaging is performed by the imaging function 144b, the DAS 118 acquires X-ray signals from the respective detection elements in the X-ray detector 112 and generates detection data.

Furthermore, the imaging function 144b performs preprocessing on the detection data output from the DAS 118. For example, the imaging function 144b performs preprocessing, such as logarithmic transformation processing, offset correction processing, inter-channel sensitivity correction processing, and beam hardening correction, on the detection data output from the DAS 118. Note that the data subjected to the pre-processing is also described as raw data. Furthermore, the detection data before the pre-processing and the raw data subjected to the pre-processing are also collectively described as projection data.

Furthermore, for example, the processing circuitry 144 reads a computer program corresponding to the acquisition function 144c from the memory 141 and executes the read computer program to acquire image data. Furthermore, for example, the processing circuitry 144 reads a computer program corresponding to the overlapping pixel summing function 144d from the memory 141 and executes the read computer program, thereby creating and/or using the energy dependent forward model. Furthermore, for example, the processing circuitry 144 reads a computer program corresponding to the output function 144e from the memory 141 and executes the read computer program, thereby outputting an image based on the overlapping pixel summation.

In the X-ray CT apparatus 10 illustrated in FIG. 1, the respective processing functions are stored in the memory 141 in the form of the computer programs executable by a computer. The processing circuitry 144 is a processor that performs a function corresponding to each computer program by reading and executing the computer program from the memory 141. In other words, the processing circuitry 144 having read the computer program has a function corresponding to the read computer program.

Note that, in FIG. 1, it has been described that the control function 144a, the imaging function 144b, the acquisition function 144c, the overlapping pixel summing function 144d, and the output function 144e are implemented by the single processing circuitry 144, but the processing circuitry 144 may be configured by combining a plurality of independent processors, and each processor may be configured to perform each function by executing each computer program. Furthermore, each processing function of the processing circuitry 144 may be performed by being appropriately distributed or integrated into a single circuit or a plurality of processing circuits.

Furthermore, the processing circuitry 144 may also perform the functions by using a processor of an external device connected via the network. For example, the processing circuitry 144 reads and executes the computer program corresponding to each function from the memory 141 and uses, as computation resources, a server group (cloud) connected to the X-ray CT apparatus 10 via the network, thereby performing each function illustrated in FIG. 1.

Furthermore, although FIG. 1 illustrates only the single memory 141, the X-ray CT apparatus 10 may include a plurality of physically separated memories. For example, the X-ray CT apparatus 10 may separately include, as the memory 141, a memory that stores a computer program required when circuitry included in the X-ray CT apparatus 10 performs its function, a memory that stores various information obtained by imaging the subject P.

Hereinafter, this point will be described with reference to FIG. 2. FIG. 2 is a block diagram illustrating an example of a configuration of an information processing system 1 according to a second embodiment. For example, the information processing system 1 includes an X-ray CT apparatus 10 and an information processing apparatus 20 as illustrated in FIG. 2. The X-ray CT apparatus 10 and the information processing apparatus 20 are connected to each other via a network NW.

Note that the location where the X-ray CT apparatus 10 and the information processing apparatus 20 are installed is arbitrary as long as they can be connected via the network NW. For example, the X-ray CT apparatus 10 and the information processing apparatus 20 may be installed within facilities different from each other. That is, the network NW may be a local network closed within the facility or a network via the Internet. Furthermore, communication between the X-ray CT apparatus 10 and the information processing apparatus 20 may be performed via another apparatus such as an image storage apparatus, or may be directly performed without using another apparatus. An example of such an image storage apparatus includes a picture archiving and communication system (PACS) server, for example.

The X-ray CT apparatus 10 illustrated in FIG. 2 has the same configuration as that of the X-ray CT apparatus 10 illustrated in FIG. 1. However, the processing circuitry 144 of the X-ray CT apparatus 10 illustrated in FIG. 2 may or may not have such functions as the acquisition function 144c and the output function 144e. Furthermore, although FIG. 2 illustrates the X-ray CT apparatus 10 as an example of a medical image diagnostic apparatus, the information processing system 1 may include a medical image diagnostic apparatus different from the X-ray CT apparatus 10. Furthermore, the information processing system 1 may include a plurality of medical image diagnostic apparatuses.

The information processing apparatus 20 performs various processes based on data acquired by the X-ray CT apparatus 10. For example, as illustrated in FIG. 2, the information processing apparatus 20 includes a memory 141, a display 142, an input interface 143, and processing circuitry 144. The display 142 can be configured similarly to the aforementioned display 142 in the apparatus 10. The information processing apparatus 20 may include a projector instead of or in addition to the display 142.

The input interface 143 can be configured similarly to the aforementioned input interface 143 of the X-ray CT apparatus 10. For example, the input interface 143 receives various input operations from a user, converts the received input operations into electrical signals, and outputs the electrical signals to the processing circuitry 144.

The processing circuitry 144 controls the overall operation of the information processing apparatus 20 by performing a control function 144a, an acquisition function 144c, and an output function 144e. For example, the control function 144a controls various functions such as the acquisition function 144c and the output function 144e based on the various input operations received from the user via the input interface 143. The acquisition function 144c is a function corresponding to the acquisition function 144c of the X-ray CT apparatus 10. The output function 144e is a function corresponding to the output function 144e of the X-ray CT apparatus 10.

In the information processing apparatus 20 illustrated in FIG. 2, respective processing functions are stored in the memory 141 in the form of computer programs that can be executed by a computer. The processing circuitry 144 is a processor that reads and executes the computer programs from the memory 141, thereby performing functions corresponding to the computer programs. In other words, the processing circuitry 144 having read the computer programs has the functions corresponding to the read computer programs. Furthermore, each processing function of the processing circuitry 144 may be performed by being appropriately distributed or integrated into a single processing circuit or a plurality of processing circuits. Furthermore, the processing circuitry 144 may also perform the functions by using a processor of an external device connected via the network NW. For example, the processing circuitry 144 reads and executes the computer programs corresponding to the functions from the memory 141 and uses, as computation resources, a server group (cloud) connected to the information processing apparatus 20 via the network NW, thereby performing the functions illustrated in FIG. 2.

Furthermore, in FIG. 1, it has been described that the single memory 141 stores the computer programs corresponding to the respective processing functions of the processing circuitry 144. Furthermore, in FIG. 2, it has been described that the single memory 144 stores the computer programs corresponding to the respective processing functions of the processing circuitry 144. However, the embodiment is not limited thereto. For example, a plurality of memories 141 may be arranged in a distributed manner, and the processing circuitry 144 may be configured to read corresponding computer programs from the individual memories 141. Furthermore, instead of storing the computer programs in the memory 141, the computer programs may be directly incorporated in the circuit of the processor. In such a case, the processor reads and executes the computer programs incorporated in the circuit to perform functions thereof.

Each component of each apparatus according to the aforementioned embodiment is functionally conceptual and does not necessarily need to be physically configured as illustrated in the drawings. That is, the specific form of distribution and integration of each apparatus is not limited to that illustrated in the drawing and all or some thereof can be functionally or physically distributed and integrated in arbitrary units according to various loads, usage conditions, and the like. Moreover, all or some of the processing functions performed by each apparatus may be performed by the CPU and the computer programs that are analyzed and executed by the CPU, or may be performed as a wired logic-based hardware.

Furthermore, the information processing method described in the aforementioned embodiment can be implemented by executing an information processing program prepared in advance on a computer such as a personal computer and a workstation. The information processing program can be distributed via a network such as the Internet. Furthermore, the information processing program can be executed by being recorded on a non-transitory computer readable recording medium such as a hard disk, a flexible disk (FD), a CD-ROM, a magneto-optical (MO) disc, and a DVD, and being read from the recording medium by the computer.

Figure 3A:
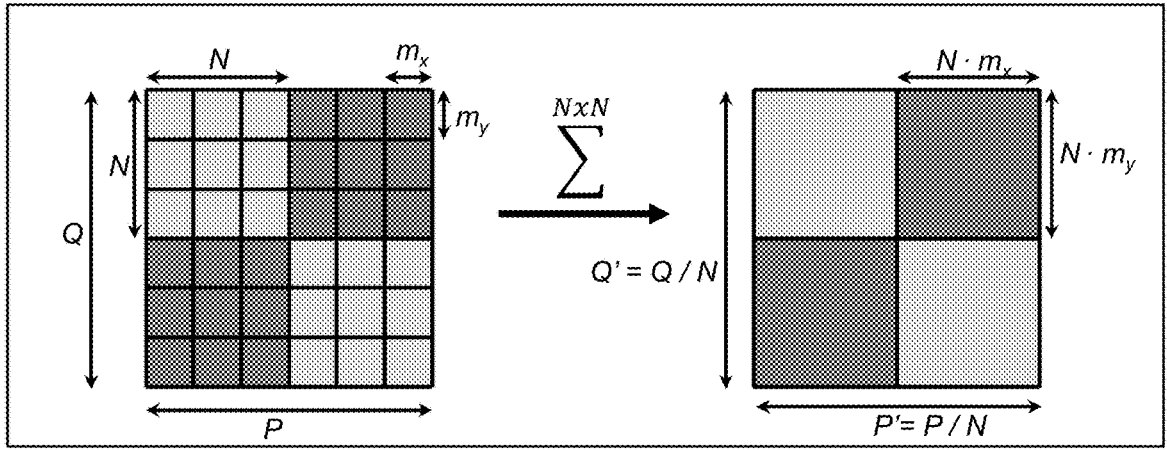
FIG. 3A is an illustration of standard pixel binning, with size N×N.

Known detector pixel binning reduces noise and improves signal-to-noise ratio in certain imaging systems under certain conditions. A standard pixel binning method consists of combining $N \times N$ groups of subpixels, each with subpixel dimension $m_x \times m_y$, to create larger virtual pixels, as shown in FIG. 3A. FIG. 3A depicts non-overlapping pixel binning where $N=3$. The detector array of FIG. 3A is of size $P \times Q$, and its binning size is $N \times N$. $N \times N$ subpixel groups are combined to produce a virtual binned detector array of size $P' \times Q'$. In CCD digital cameras, for example, typically $2 \times 2$ or $3 \times 3$ groups of subpixels are combined to create a larger less noisy pixel. Standard pixel binning has been described for integrated detector x-ray systems. Known PCCT systems have implemented standard pixel binning up to $4 \times 4$.

Figure 3B:
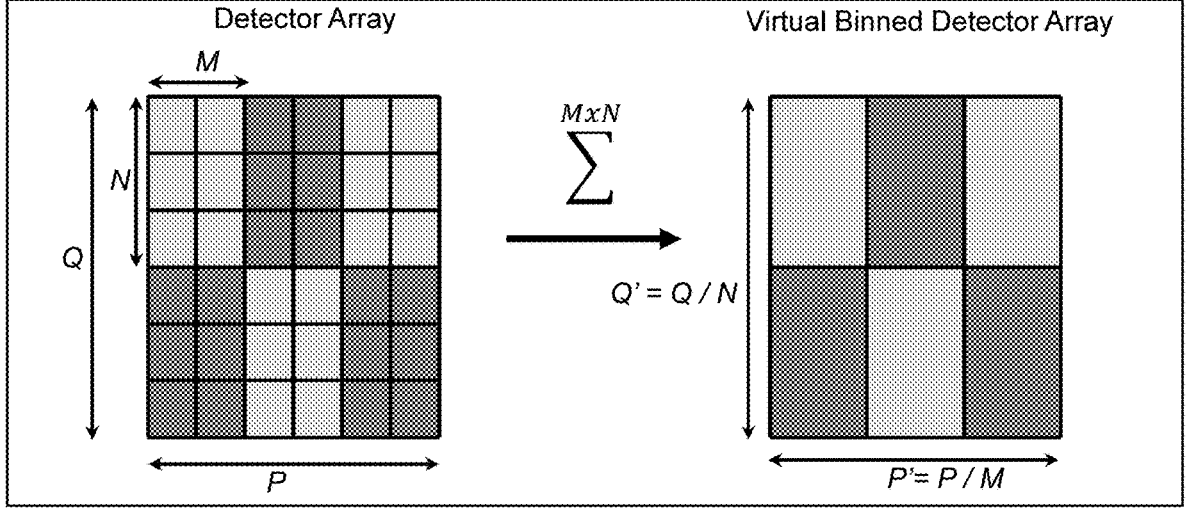
FIG. 3B is an illustration of standard pixel binning, with asymmetrical sizing M×N.

The subpixel grouping does not have to be square, and rectangular or asymmetrical $N \times M$ subpixel groups can be implemented as well. FIG. 3B depicts asymmetrical pixel binning where $M \times N = 2 \times 3$. Here the pitch and number of subpixels in the column (also called channel) direction is two, and the number of subpixels in the row (also called segment) direction is three.

Figure 4:
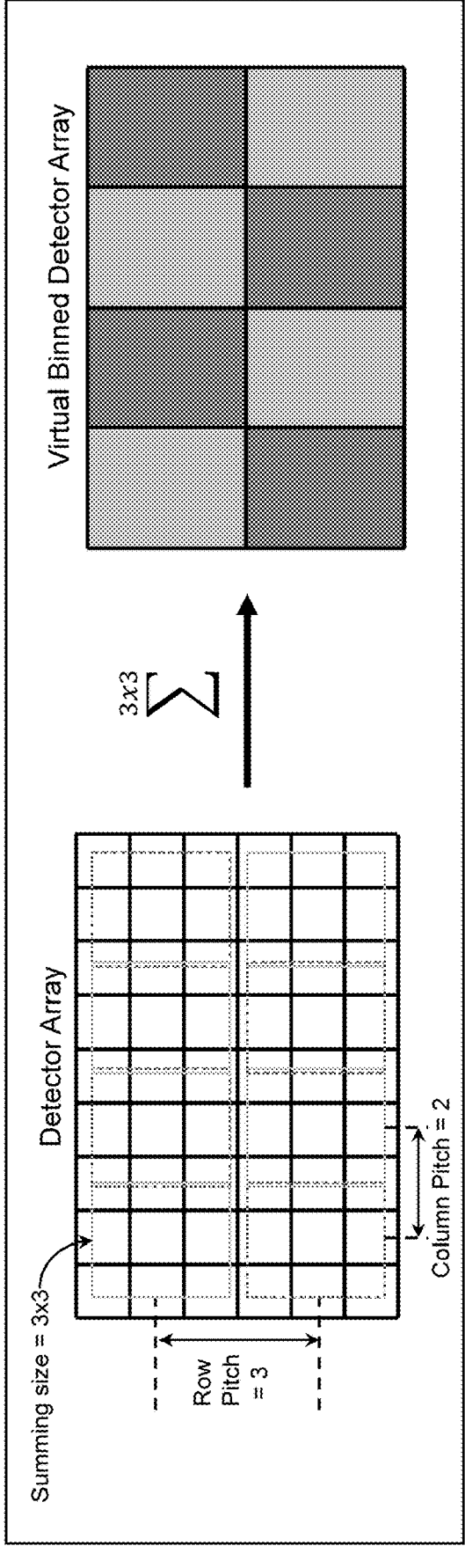
FIG. 4 is an illustration of overlapping pixel binning with symmetrical summing size N×N and overlap in the channel (column) direction only.
Figure 6A:
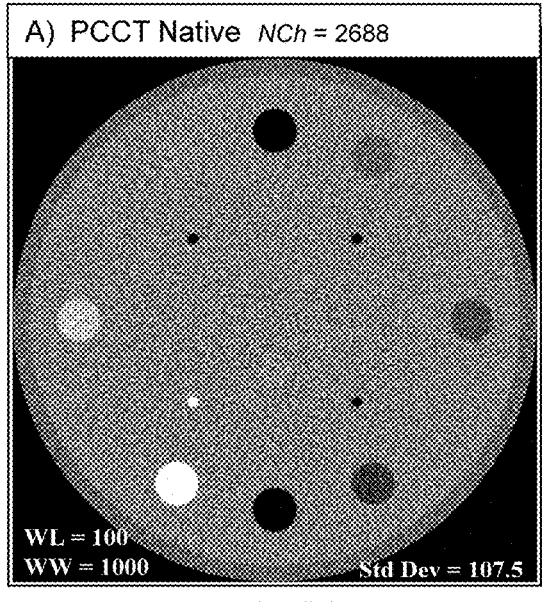
FIGS. 6A-6D show reconstructions with the native channels and the three binning methods of FIGS. 5A-5C.
Figure 6B:
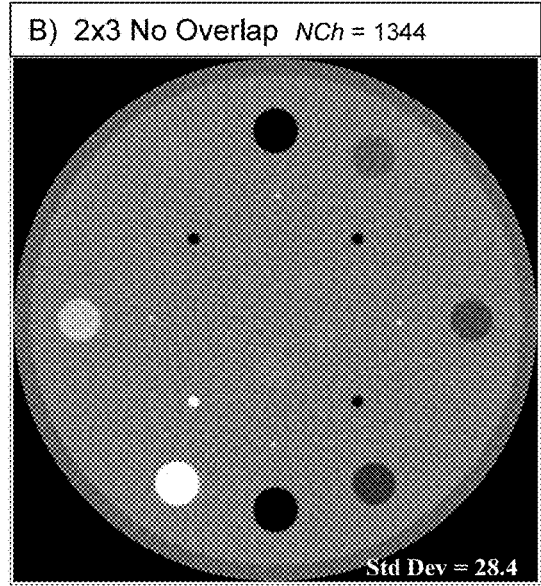
Figure 6C:
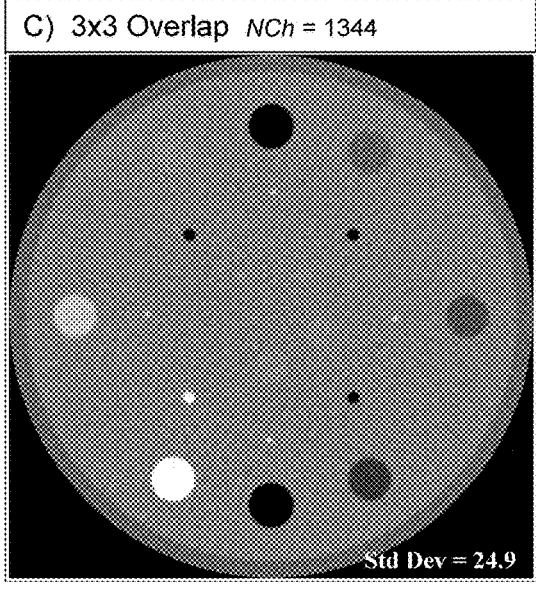
Figure 6D:
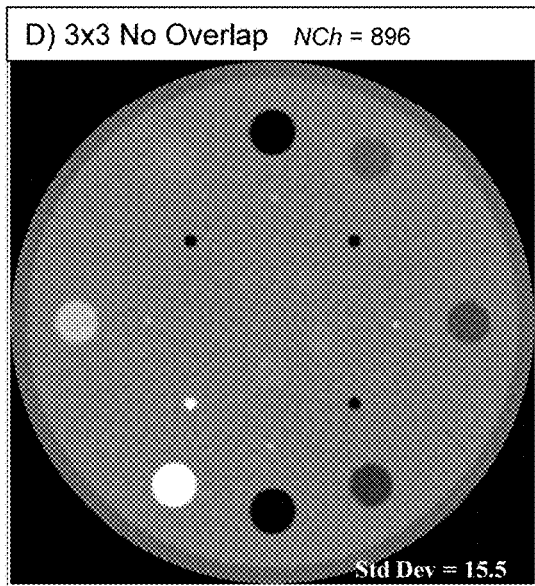
Figure 6E:
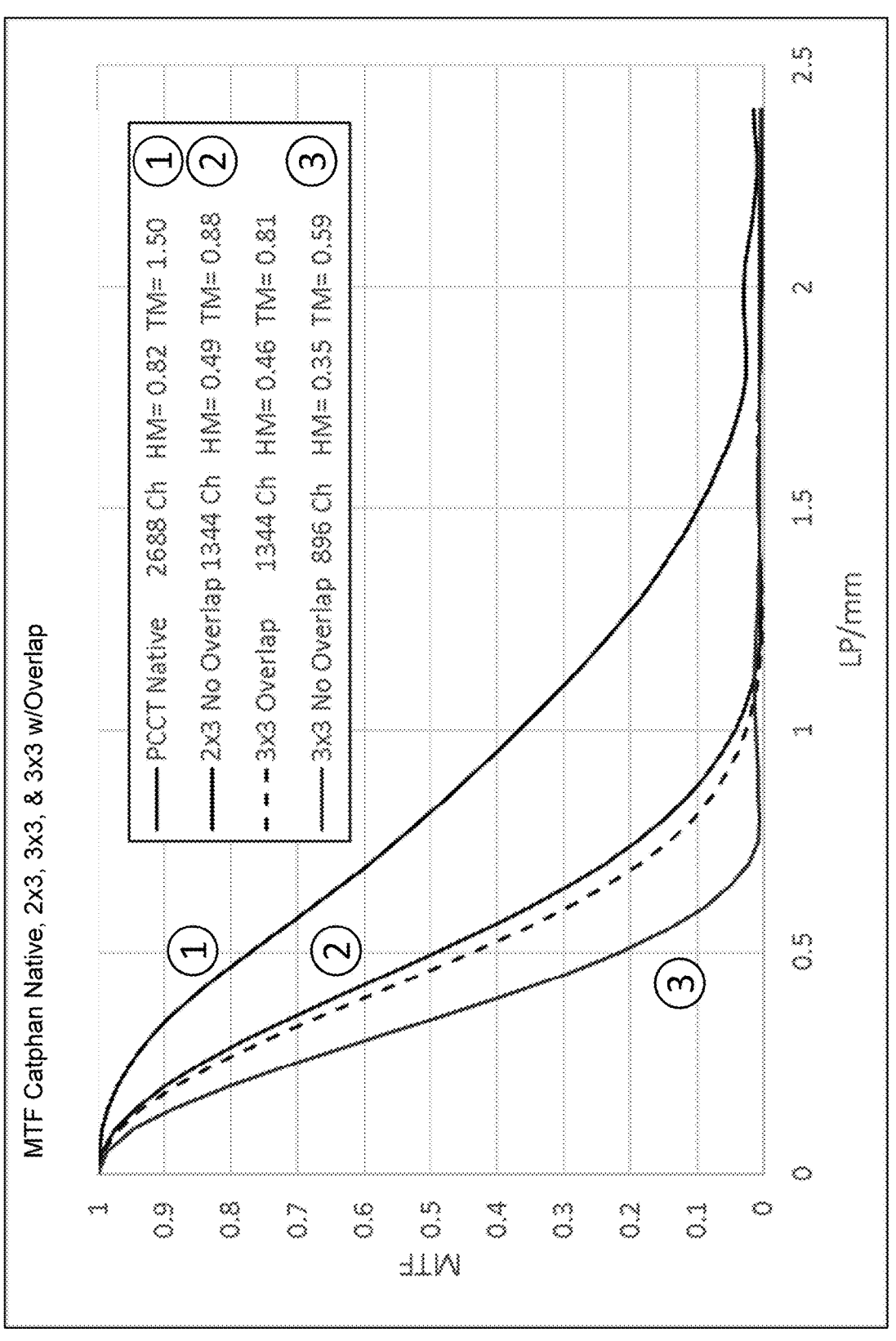
FIG. 6E shows the corresponding MTF curves.

According embodiments described herein, pixel binning can be performed by using an overlapping summing scheme to be applied on PCD CT systems with small pixels. When combining the subpixels to a large size at a pitch that is less than the summing size, spatial resolution is improved compared to the summing size without overlap by trading off the noise performance. The additional benefits are a more robust projection measurement and less image quality problems associated with photon starvation. FIG. 4 shows an example of an overlapping pixel binning structure. It utilizes a $3 \times 3$ subpixel summation, as in FIG. 3A, but with a column pitch of two and row pitch of three, like the $2 \times 3$ binning in FIG. 3B. In this case, one of the three columns contributes to both the left and right neighbouring summed pixels. In an embodiment, the row pitch is equal to the group subpixel group matrix size, hence the overlap is only in the column (channel) direction. To achieve this configuration, the PCD array is configured to include (a) a first micro-pixel area including a first group of plural micro-pixels of the plurality of micro-pixels (indicated as the first $3 \times 3$ group encircled by a solid line) and (b) a second micro-pixel area including a second group of plural micro-pixels of the plurality of micro-pixels (indicated as the first $3 \times 3$ group encircled by a dashed line), such that a portion of the first and second groups of plural micro-pixels overlap between the first and second groups as shown by those pixels encircled by both a solid line and a dashed line. FIG. 4 shows 8 micro-pixel areas with 6 overlapping regions encircled by both a solid line and a dashed line.

This configuration of the PCD array can be performed virtually after the raw data has been collected from the array, or the PCD array can be configured with summing circuitry configured to perform the PCD array configuration and summing using virtual bins as discussed below based on the PCD array receiving configuration information describing the layout where the configuration information is sent from a connected processor.

A PCCT system requires calibration and generation of calibration tables for the forward response. According to an embodiment, the calibration, generation of the calibration tables, and the summing scheme for calibration are matched to those used for imaging. Referring now to FIGS. 5A, 5B, and 5C, FIGS. 5A and 5B illustrate the standard pixel binning (3×3 and 2×3, respectively), while FIG. 5C illustrates an overlapping pixel scheme for a 3×3 pixel-array with overlap, according to one embodiment. Here, $Ch_{in}(n)$ is input unbinned data, and $Ch_{out}(m)$ is the resulting output binned data. In each case, the total number of input channels is $NCh_{in}$, and the total number of binned output channels is $NCh_{out}$. The 3×3 scheme without overlap (FIG. 5A) yields $NCh_{out}$ evenly spaced with respect to $NCh_{in}$, such that $$NCh_{out} = \frac{NCh_{in}}{3}.$$

The 2×3 scheme without overlap (FIG. 5B) also yields $NCh_{out}$ evenly spaced with respect to $NCh_{in}$, such that $$NCh_{out} = \frac{NCh_{in}}{2}.$$

FIG. 5C depicts how the 3×3 overlap scheme (with column pitch=2) changes the output. In FIG. 5C, $$NCh_{out} = \frac{NCh_{in}}{2},$$

but for even $NCh_{in}$, there will be a missing column, and output channels $NCh_{out}$ will be offset with respect to $NCh_{in}$. In the embodiment of FIG. 5C, the pixels are summed with equal weighting, and the spatial resolution versus noise reduction is achieved by the amount of overlap, not weighting. Thus, the embodiment of FIG. 5C provides an advantage that the overlap provides better resolution for similar noise reduction compared to non-overlap binning or filtering. In an alternate embodiment, the summing can be further weighted so that center channels are weighted more to enhance spatial resolution. Additionally, the QQ offset is adjusted to compensate for the missing column.

FIGS. 6A-6D depict the reconstruction results of the native and the three binning methods discussed with respect to FIGS. 5A-5C, and FIG. 6E depicts the corresponding Modulation Transfer Function (MTF) curves. Here, the pixels are summed without weighting. The 3×3 with overlap yields similar resolution to the 2×3 without overlap, but the 3×3 with overlap has better noise performance. An advantage of overlapping pixel summing is that when subpixels are combined at a pitch that is less than the summing size extra spatial resolution can be gained with smaller loss in noise performance. Overlapping pixel summing also offer more flexibility in determining the spatial resolution versus noise performance which comes from the ability to vary the amount of overlap.

Figure 7:
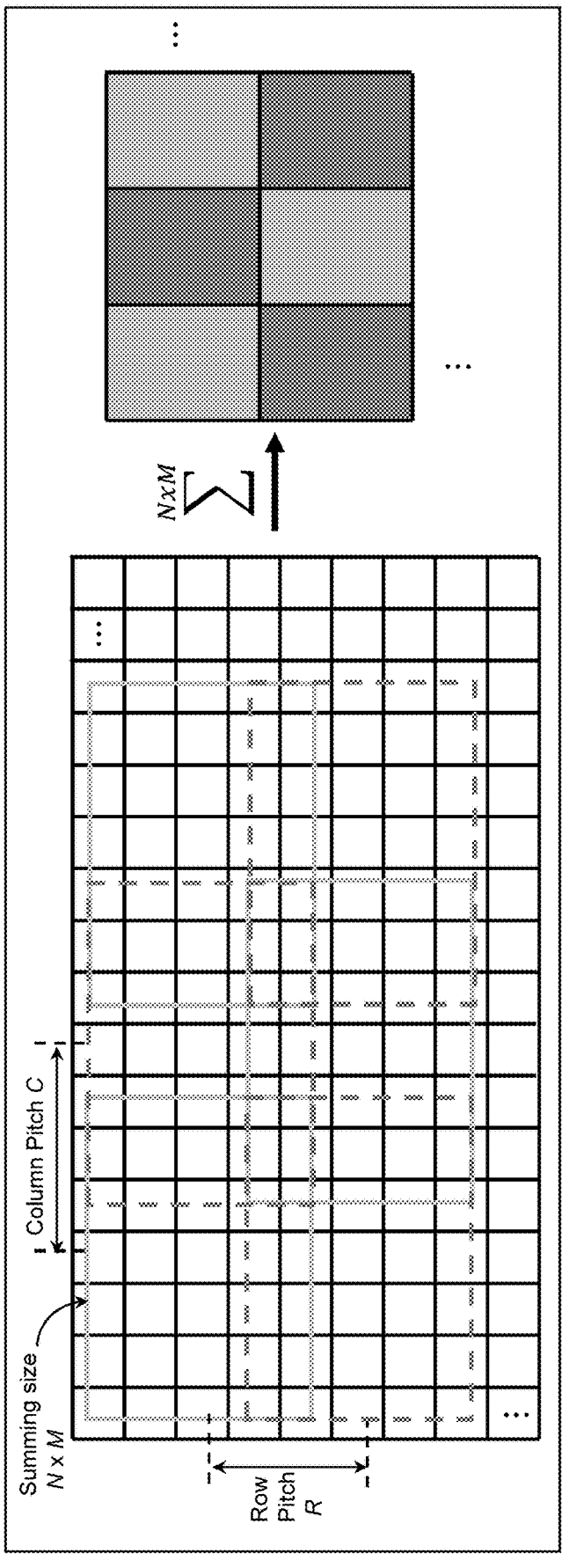
FIG. 7 shows a general example of overlapping pixel summation for a M×N summing size with row pitch R and column pitch C.
Figure 8:
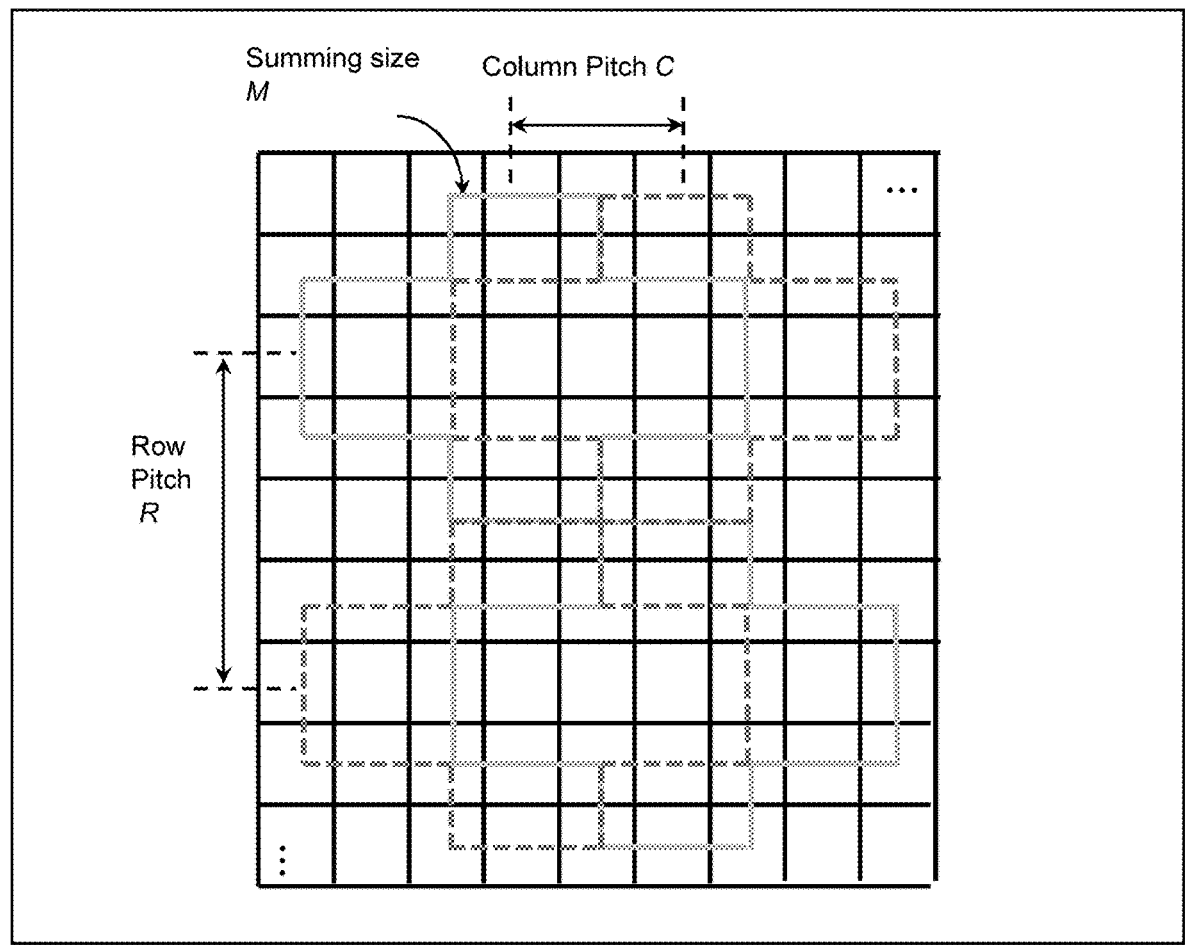
FIG. 8 depicts an overlapping pixel summation for a non-rectangular shape.

The embodiment described above (3×3 with column pitch=2) is only one example of possible overlapping pixel summing schemes. Alternate summing scheme embodiments can include any summing size M×N, any column pitch C, any row pitch R, any overlap in the column direction, any overlap in the row direction, and any overlap in both the column and row directions. FIG. 7 shows a generic example where the embodiments can be implemented by varying N, M C, and R. Other embodiments include the previous embodiments, but include non-rectangular summing sizes, such as a cross as depicted in FIG. 8.

In an embodiment, more than one overlapping scheme is implemented. An example of when using more than one overlapping scheme could be useful is when a system has options for imaging at different resolutions and each resolution may require a different overlapping summing scheme. Another example could be when different detectors are used, like differing charge sharing and crosstalk effects, different overlapping summing schemes may need to be used. Additionally, multiple overlapping summing schemes may be required when sensor materials are not uniform or for other detection system complexities that do not allow for accurate modeling of the photon counting detector response and different calibration schemes are used to calibrate the forward model. Another factor that may required multiple overlapping summing schemes is when an anti-scatter grid is implemented with the detector.

The overlapping pixel summing scheme is not limited to PCCT detectors or systems. The scheme can be applied to any type of detector or imaging system including x-ray integrating non-PCCT, optical cameras, acoustic sensors, and nuclear imaging.

The use of overlapping pixel summing schemes compared to standard pixel binning can result in improved spatial resolution with less of a tradeoff in noise performance, improved image quality by reducing degrading effects of sensor material non-uniformity, improved image quality by reducing degrading effects due to photon counting detection physics in semiconductor materials such as charge sharing, k-escape, and scattering, and improved image quality by reducing the degrading effects of shadow of anti-scatter grid.

The term "processor" used in the above description, for example, means a circuit such as a CPU, a graphics processing unit (GPU), an application specific integrated circuit (ASIC), and a programmable logic device (for example, a simple programmable logic device (SPLD), a complex programmable logic device (CPLD), and a field programmable gate array (FPGA)). When the processor is, for example, the CPU, the processor performs functions by reading and executing computer programs stored in a storage circuit. On the other hand, when the processor is, for example, the ASIC, the functions are directly incorporated in the circuit of the processor as a logic circuit instead of storing the computer programs in the storage circuit. Note that each processor of the embodiment is not limited to a case where each processor is configured as a single circuit, and one processor may be configured by combining a plurality of independent circuits to perform functions thereof. Moreover, a plurality of components in each drawing may be integrated into one processor to perform functions thereof.

Additional embodiments are provided by way of example in the following parentheticals:

(1) A photon counting detector (PCD) apparatus including, but not limited to: (a) a PCD array including a plurality of micro-pixels positioned in at least one of a channel direction and a row direction; and (b) processing circuitry configured to: receive signals from each of the plurality of micro-pixels, configure the PCD array to include (a) a first micro-pixel area including a first group of plural micro-pixels of the plurality of micro-pixels and (b) a second micro-pixel area including a second group of plural micro-pixels of the plurality of micro-pixels, such that a portion of the first and second groups of plural micro-pixels overlap between the first and second groups, bin the signals from the first group of plural micro-pixels into a first virtual bin value; and bin the signals from the second group of plural micro-pixels into a second virtual bin value.

(2) The photon counting detector (PCD) apparatus according to (1), wherein the first and second micro-pixels are each n by m arrays of micro-pixels where m and n are each integers greater than 1, and wherein the overlap between the first and second groups is m or n micro-pixels.

(3) The photon counting detector (PCD) apparatus according to (1), wherein the first and second micro-pixels are each n by n arrays of micro-pixels where n is an integer greater than 1, and wherein the overlap between the first and second groups is n micro-pixels.

(4) The photon counting detector (PCD) apparatus according to (2), wherein the processing circuitry is further configured to reconfigure the PCD array such that the first and second micro-pixels are each p by q arrays of micro-pixels where p and q are each integers greater than 1 and p and q are not equal to either n and m or m an n.

(5) The photon counting detector (PCD) according to (2), wherein n and m are 2 and 3, respectively, and p and q are 3 and 3, respectively.

(6) The photon counting detector (PCD) apparatus according to (1), wherein the first and second micro-pixels are each non-rectangular.

(7) The photon counting detector (PCD) apparatus according to any one of (1)-(6), wherein processing circuitry configured to configure the PCD array are configured to configure the PCD array prior to receiving the signals from each of the plurality of micro-pixels.

(8) The photon counting detector (PCD) apparatus according to any one of (1)-(6), wherein processing circuitry configured to configure the PCD array are configured to configure the PCD array after receiving the signals from each of the plurality of micro-pixels.

(9) An overlapping micro-pixel summing method including, but not limited to: configuring a PCD array including a plurality of micro-pixels positioned in at least one of a channel direction and a row direction to include a first micro-pixel area including a first group of plural micro-pixels of the plurality of micro-pixels and a second micro-pixel area including a second group of plural micro-pixels of the plurality of micro-pixels, such that a portion of the first and second groups of plural micro-pixels overlap between the first and second groups; receiving signals from each of the plurality of micro-pixels; binning the signals from the first group of plural micro-pixels into a first virtual bin value; and binning the signals from the second group of plural micro-pixels into a second virtual bin value.

(10) The method according to (9), wherein the first and second micro-pixels are each n by m arrays of micro-pixels where m and n are each integers greater than 1, and wherein the overlap between the first and second groups is m or n micro-pixels.

(11) The method according to (9), wherein the first and second micro-pixels are each n by n arrays of micro-pixels where n is an integer greater than 1, and wherein the overlap between the first and second groups is n micro-pixels.

(12) The method according to (10), further including reconfiguring the PCD array such that the first and second micro-pixels are each p by q arrays of micro-pixels where p and q are each integers greater than 1 and p and q are not equal to either n and m or m an n.

(13) The method according to (10), wherein n and m are 2 and 3, respectively, and p and q are 3 and 3, respectively.

(14) The method according to (9), wherein the first and second micro-pixels are each non-rectangular.

(15) The method according to any one of (9)-(14), wherein the PCD array is configured prior to receiving the signals from each of the plurality of micro-pixels.

(16) The method according to any one of (9)-(14), wherein the PCD array is configured after receiving the signals from each of the plurality of micro-pixels.

(17) A computer program product including, but not limited to:
a non-transitory computer readable medium including computer instructions stored therein, wherein the computer instructions, when executed by a computer processor, cause the computer processor to perform the steps of: configuring a PCD array including a plurality of micro-pixels positioned in at least one of a channel direction and a row direction to include a first micro-pixel area including a first group of plural micro-pixels of the plurality of micro-pixels and a second micro-pixel area including a second group of plural micro-pixels of the plurality of micro-pixels, such that a portion of the first and second groups of plural micro-pixels overlap between the first and second groups; receiving signals from each of the plurality of micro-pixels; binning the signals from the first group of plural micro-pixels into a first virtual bin value; and binning the signals from the second group of plural micro-pixels into a second virtual bin value.

(18) The computer program product according to (17), wherein the first and second micro-pixels are each n by m arrays of micro-pixels where m and n are each integers greater than 1, and wherein the overlap between the first and second groups is m or n micro-pixels.

(19) The computer program product according to (17), wherein the first and second micro-pixels are each n by n arrays of micro-pixels where n is an integer greater than 1, and wherein the overlap between the first and second groups is n micro-pixels.

(20) The computer program product according to (18), further including computer instructions for reconfiguring the PCD array such that the first and second micro-pixels are each p by q arrays of micro-pixels where p and q are each integers greater than 1 and p and q are not equal to either n and m or m an n.

(21) The computer program product according to (18), wherein n and m are 2 and 3, respectively, and p and q are 3 and 3, respectively.

(22) The computer program product according to (17), wherein the first and second micro-pixels are each non-rectangular.

(23) The computer program product according to any one of (17)-(22), wherein the PCD array is configured prior to receiving the signals from each of the plurality of micro-pixels.

(24) The computer program product according to any one of (17)-(22), wherein the PCD array is configured after receiving the signals from each of the plurality of micro-pixels.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A photon counting detector (PCD) apparatus, comprising:

a PCD array including a plurality of micro-pixels positioned in at least one of a channel direction and a row direction; and processing circuitry configured to:

receive signals from each of the plurality of micro-pixels, configure the PCD array to include (a) a first micro-pixel area including a first group of plural micro-pixels of the plurality of micro-pixels, and (b) a second micro-pixel area including a second group of plural micro-pixels of the plurality of micro-pixels, such that a portion of the first and second groups of plural micro-pixels overlap between the first and second groups, bin the signals from the first group of plural micro-pixels into a first virtual bin value by summing the signals from the first group with equal weighting in a spatial domain;

bin the signals from the second group of plural micro-pixels into a second virtual bin value by summing the signals from the second group with the equal weighting in the spatial domain;

combine the first and second virtual bin values to generate a combined data set; and generate an image by performing reconstruction on the combined data set.

2. The photon counting detector (PCD) apparatus of claim 1, wherein the first and second groups of micro-pixels are each n by m arrays of micro-pixels, where m and n are each integers greater than 1, and wherein the overlap between the first and second groups is m or n micro-pixels.

3. The photon counting detector (PCD) apparatus according to claim 2, wherein the processing circuitry is further configured to reconfigure the PCD array such that the first and second micro-pixels are each p by q arrays of micro-pixels, where p and q are each integers greater than 1, and p and q are not equal to either n and m, or m and n, respectively.

4. The photon counting detector (PCD) apparatus according to claim 3, wherein n and m are 2 and 3, respectively, and p and q are 3 and 3, respectively.

5. The photon counting detector (PCD) apparatus according to claim 1, wherein the first and second groups of micro-pixels are each n by n arrays of micro-pixels, where n is an integer greater than 1, and wherein the overlap between the first and second groups is n micro-pixels.

6. The photon counting detector (PCD) apparatus according to claim 1, wherein the first and second groups of micro-pixels are each non-rectangular.

7. The photon counting detector (PCD) apparatus according to claim 1, wherein the processing circuitry is further configured to configure the PCD array prior to receiving the signals from each of the plurality of micro-pixels.

8. The photon counting detector (PCD) apparatus according to claim 1, wherein the processing circuitry is further configured to configure the PCD array after receiving the signals from each of the plurality of micro-pixels.

9. An overlapping micro-pixel summing method, comprising:

configuring a PCD array including a plurality of micro-pixels positioned in at least one of a channel direction and a row direction to include a first micro-pixel area including a first group of plural micro-pixels of the plurality of micro-pixels and a second micro-pixel area including a second group of plural micro-pixels of the plurality of micro-pixels, such that a portion of the first and second groups of plural micro-pixels overlap between the first and second groups;

receiving signals from each of the plurality of micro-pixels;

binning the signals from the first group of plural micro-pixels into a first virtual bin value by summing the signals from the first group with equal weighting in a spatial domain;

binning the signals from the second group of plural micro-pixels into a second virtual bin value by summing the signals from the second group with the equal weighting in the spatial domain;

combining the first and second virtual bin values to generate a combined data set; and generating an image by performing reconstruction on the combined data set.

10. The method according to claim 9, wherein the first and second groups of micro-pixels are each n by m arrays of micro-pixels, where m and n are each integers greater than 1, and wherein the overlap between the first and second groups is m or n micro-pixels.

11. The method according to claim 10, further comprising reconfiguring the PCD array such that the first and second micro-pixels are each p by q arrays of micro-pixels, where p and q are each integers greater than 1, and p and q are not equal to either n and m, or m and n, respectively.

12. The method according to claim 11, wherein n and m are 2 and 3, respectively, and p and q are 3 and 3, respectively.

13. The method according to claim 9, wherein the first and second groups of micro-pixels are each n by n arrays of micro-pixels, where n is an integer greater than 1, and wherein the overlap between the first and second groups is n micro-pixels.

14. The method according to claim 9, wherein the first and second groups of micro-pixels are each non-rectangular.

15. The method according to claim 9, wherein the PCD array is configured prior to receiving the signals from each of the plurality of micro-pixels.

16. The method according to claim 9, wherein the PCD array is configured after receiving the signals from each of the plurality of micro-pixels.

17. A computer program product including a non-transitory computer-readable medium including computer instructions stored therein, wherein the computer instructions, when executed by processing circuitry, cause the processing circuitry to perform:

configuring a PCD array including a plurality of micro-pixels positioned in at least one of a channel direction and a row direction to include a first micro-pixel area including a first group of plural micro-pixels of the plurality of micro-pixels and a second micro-pixel area including a second group of plural micro-pixels of the plurality of micro-pixels, such that a portion of the first and second groups of plural micro-pixels overlap between the first and second groups;

receiving signals from each of the plurality of micro-pixels;

binning the signals from the first group of plural micro-pixels into a first virtual bin value by summing the signals from the first group with equal weighting in a spatial domain;

binning the signals from the second group of plural micro-pixels into a second virtual bin value by summing the signals from the second group with the equal weighting in the spatial domain;

combining the first and second virtual bin values to generate a combined data set; and generating an image by performing reconstruction on the combined data set.

18. The computer program product according to claim 17, wherein the first and second groups of micro-pixels are each n by m arrays of micro-pixels, where m and n are each integers greater than 1, and wherein the overlap between the first and second groups is m or n micro-pixels.

19. The computer program product according to claim 18, further comprising computer instructions for reconfiguring the PCD array such that the first and second groups of micro-pixels are each p by q arrays of micro-pixels, where p and q are each integers greater than 1, and p and q are not equal to either n and m, or m and n, respectively.

20. The computer program product according to claim 17, wherein the first and second groups of micro-pixels are each n by n arrays of micro-pixels, where n is an integer greater than 1, and wherein the overlap between the first and second groups is n micro-pixels.

21. A photon counting detector (PCD) apparatus, comprising:

a PCD array including a plurality of micro-pixels positioned in at least one of a channel direction and a row direction; and processing circuitry configured to receive signals from each of the plurality of micro-pixels, configure the PCD array to include (a) a first micro-pixel area including a first group of plural micro-pixels of the plurality of micro-pixels, and (b) a second micro-pixel area including a second group of plural micro-pixels of the plurality of micro-pixels, such that a portion of the first and second groups of plural micro-pixels overlap between the first and second groups, bin the signals from the first group of plural micro-pixels into a first virtual bin value with a weighting so that center channels micro-pixels are weighted more than micro-pixels in the portion; and bin the signals from the second group of plural micro-pixels into a second virtual bin value with a weighting so that center channels micro-pixels are weighted more than micro-pixels in the portion.

* * * * *